United States Patent
Fuchs et al.

(10) Patent No.: US 7,157,598 B2
(45) Date of Patent: Jan. 2, 2007

(54) METHOD FOR PRODUCING AN AQUEOUS ALKALI ACRYLATE SOLUTION

(75) Inventors: Eberhard Fuchs, Frankenthal (DE); Hans Martan, Frankenthal (DE); Klaus Joachim Mueller-Engel, Stutensee (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 107 days.

(21) Appl. No.: 10/510,236

(22) PCT Filed: May 2, 2003

(86) PCT No.: PCT/EP03/04602

§ 371 (c)(1),
(2), (4) Date: Oct. 14, 2004

(87) PCT Pub. No.: WO03/095410

PCT Pub. Date: Nov. 20, 2003

(65) Prior Publication Data

US 2005/0096445 A1 May 5, 2005

(30) Foreign Application Priority Data

May 7, 2002 (DE) .............................. 102 20 494

(51) Int. Cl.
C07C 57/02 (2006.01)
C07C 51/42 (2006.01)
(52) U.S. Cl. ...................... 562/598; 562/600
(58) Field of Classification Search ............... 562/512, 562/599, 600
See application file for complete search history.

(56) References Cited

U.S. PATENT DOCUMENTS 4,219,389 A * 8/1980 Biola et al. ............... 203/72
4,340,706 A * 7/1982 Obayashi et al. .......... 526/207

FOREIGN PATENT DOCUMENTS

| DE | 12 05 502 | 11/1965 |
|----|-----------|---------|
| DE | 21 36 396 | 2/1973 |
| DE | 29 43 707 | 5/1980 |
| DE | 34 32 082 | 3/1986 |
| DE | 3432082 | * 3/1986 |
| DE | 197 40 253 | 3/1999 |
| DE | 101 22 027 | 5/2002 |
| DE | 101 31 297 | 1/2003 |
| EP | 0 117 146 | 8/1984 |
| EP | 0 293 224 | 11/1988 |
| EP | 0 297 445 | 1/1989 |
| GB | 1 450 986 | 9/1976 |
| JP | 50 142511 | 11/1975 |

OTHER PUBLICATIONS

Ullmann's Encyclopedia of Ind. Chem. 5$^{th}$ Ed. On CD-Rom, "Acrylic Acid and Derivatives, 1.3.1 Propenoxidation", Wiley-VCH Weinheim 1997.
Weissermel, Klaus et al. "Industrielle Organische Chemie", 4. Auflage, VCH Verlagsgesellschaft, Weinheim. pp. 315-317 1994.

* cited by examiner

*Primary Examiner*—Thurman K. Page
*Assistant Examiner*—Karl Puttlitz
(74) *Attorney, Agent, or Firm*—Oblon, Spivak, McClelland, Maier & Neustadt, P.C.

(57) ABSTRACT

A process prepares an aqueous alkali metal acrylate solution by distillatively removing acrylic acid from a mixture as vapors and taking up the vapors immediately from the gas phase into an aqueous alkali solution.

16 Claims, No Drawings

METHOD FOR PRODUCING AN AQUEOUS ALKALI ACRYLATE SOLUTION

The present invention relates to a process for preparing an aqueous alkali metal acrylate solution by distillatively removing acrylic acid from an acrylic acid-containing mixture and generating an aqueous alkali metal acrylate solution from the distillatively removed acrylic acid and an aqueous solution of a basic alkali metal salt.

In this document, the term alkali metal acrylate refers to the alkali metal salts of acrylic acid.

An aqueous alkali metal acrylate solution refers to an aqueous solution which comprises at least one dissolved alkali metal acrylate.

Acrylic acid is generally produced by heterogeneously catalyzed gas phase oxidation of propene or propane using molecular oxygen (cf., for example, Ullmann's Encyclopedia of Ind. Chem. 5th ed. on CD-ROM, "Acrylic acid and derivatives, 1.3.1 Propene oxidation", Wiley-VCH Weinheim, 1997; K. Weisärmel, H.-J. Arpe "Industrielle Org. Chem.", 4th edition, VCH Verlagsgesellschaft, Weinheim 1994, p. 315–17 and also DE-A 2943707, DE-C 1205502, EP-A 117146, EP-A 293224, GB-A 1450986, DE-A 10131297 and DE-A 10122027).

The product gas mixture resulting from a heterogeneously catalyzed gas phase oxidation comprises, as well as the main component acrylic acid, secondary components, for example, acetic acid and propionic acid, a series of aldehydes, for example furfurals, benzaldehyde, formaldehyde, acrolein, acetaldehyde and propionaldehyde, and also protoanemonin and various unsaturated or aromatic carboxylic acids and their anhydrides, for example benzoic acid, maleic acid, maleic anhydride and phthalic anhydride.

The majority of these secondary components prove disadvantageous in the subsequent use of acrylic acid.

This is true in particular when the intention is to use the acrylic acid for preparing water-absorbing resins.

As is well known, water-absorbing resins based on acrylic acid are prepared predominantly by free radical polymerization of aqueous monomer solutions which substantially comprise acrylic acid as the free radically polymerizable monomer, and at least a portion of the acrylic acid is generally present in the aqueous monomer solution as dissolved alkali metal acrylate. In this context, monomers are quite generally chemical compounds which have at least one ethylenically unsaturated double bond. The polymerization itself may be carried out, for example, as a solution or as a gel polymerization in a homogeneous aqueous phase or else as a suspension polymerization in which the aqueous monomer solution forms the disperse phase. The hydrogels obtainable in this manner are generally subsequently surface postcrosslinked. In dried form, they then form powders which have a marked ability to absorb water and find use, for example, in diapers or hygiene articles. In this context, they are also known as superabsorbers.

The abovementioned secondary components may thus not only negatively influence the polymerization procedure as such (they may, for example, negatively influence the polymerization rate or the magnitude of the polymer molecular weight), but their presence in superabsorbers ready for use is generally also undesired.

Starting from the product gas mixture from a heterogeneously catalyzed gas phase oxidation, an aqueous alkali metal acrylate solution which is suitable for producing superabsorbers is customarily prepared in such a manner that secondary components contained in the product gas mixture are at least partially removed from the acrylic acid.

To this end, the prior art discloses numerous processes. For example, a basic separation of the acrylic acid from the product gas mixture may be carried out by taking up the acrylic acid absorptively in a suitable absorbent (for example water or a mixture of from 70 to 75% by weight of diphenyl ether and from 25 to 30% of diphenyl) to obtain an acrylic acid-containing absorbate (cf., for example, EP-A 297445 and DE-C 2136396). Subsequent, predominantly distillative separating processes then allow acrylic acid which has an increased purity to be removed from the absorbate. Alternatively, the product gas mixture from the gas phase oxidation may also be fractionally condensed, as described, for example, by DE-A 19740253. The already comparatively pure acrylic acid withdrawn may, after optional intermediate crystallizing purification, be further distillatively purified according to their need.

The acrylic acid having increased purity obtainable in this manner is customarily admixed with a storage polymerization inhibitor (for example hydroquinone monomethyl ether) which has the purpose of suppressing uncontrolled, undesired, premature free radical polymerization taking place in the solution in the acrylic acid.

Acrylic acid is stored thus prepared in storage tanks and used as required for producing superabsorbers. To this end, a polymerizable aqueous alkali metal acrylate solution is generated from the polymerization-inhibited acrylic acid and an aqueous solution of a basic alkali metal salt and optionally other components. The addition of polymerization initiator (for example peroxide compounds) and the optional influence of elevated temperatures customarily then sets off the free radical polymerization in order to generate the superabsorbing alkali metal polyacrylate.

A disadvantage of the above-described procedure is that the polymerization initiator used and the storage polymerization inhibitor contained in the acrylic acid are antagonists. It is a further disadvantage that during acrylic acid storage, it adds to itself by Michael addition to form acrylic acid oligomers, of which diacrylic acid is the most significant for statistical reasons. These acrylic acid oligomers are disadvantageous in particular in that they dissociate at elevated temperature to give monomeric acrylic acid. In other words, when they are copolymerized, this may lead, after the end of the polymerization and removal of the remaining, nonpolymerized monomers, to the resulting polymer again containing residual monomeric acrylic acid, which is undesired and toxicologically not entirely acceptable. Frequently, the stored acrylic acid will therefore be again subjected to distillative purification before its use.

It is an object of the present invention to provide an improved process for preparing an aqueous alkali metal acrylate solution by distillatively removing acrylic acid from an acrylic acid-containing mixture and then generating an aqueous alkali metal acrylate solution from the distillatively removed acrylic acid and an aqueous solution of a basic alkali metal salt, which only exhibits the above-mentioned disadvantages to a limited extent, if at all.

We have found that this object is achieved by a process for preparing an aqueous alkali metal acrylate solution by distillatively removing acrylic acid from an acrylic acid-containing mixture and generating an aqueous alkali metal acrylate solution from the distillatively removed acrylic acid and an aqueous solution of a basic alkali metal salt, which comprises a) feeding the acrylic acid-containing mixture to a distillation apparatus,
b) carrying out the removal of the acrylic acid from the acrylic acid-containing mixture in the distillation apparatus above the feed point and
c) generating the aqueous alkali metal acrylate solution in such a manner that the acrylic acid removed in the distillation apparatus is taken up immediately from the gas phase into an aqueous solution of an alkali metal hydroxide, an alkali metal carbonate and/or an alkali metal hydrogencarbonate.

Useful alkali metal hydroxides, carbonates and/or hydrogencarbonates for the process according to the invention are in particular the appropriate salts of sodium, potassium or a mixture of these two metals.

Among the group of the abovementioned salts, preference is given according to the invention to the sodium salts over the potassium salts. Among the group of the abovementioned salts, preference is further given according to the invention to the hydroxides. In other words, particular preference is given according to the invention to an aqueous sodium hydroxide solution.

According to the invention, the term "distillative removal" should be understood in its widest sense and encompass both a simple distillation, i.e. a distillation in which essentially no condensed phase is passed in countercurrent to the rising vapor, and also a rectification in which the condensed phase is passed in countercurrent to the rising vapor and participates in extensive mass transfer with it.

The removal of acrylic acid according to the invention may be realized in a simple manner, for example, by carrying out the removal above a chimney tray mounted in the distillation apparatus. The chimney tray is configured in such a manner that although gas phases can rise through the chimney, no liquid phase can ref lux through it into the distillation apparatus.

In the space above the chimney opening which will generally be roofed, the aqueous solution of an alkali metal hydroxide, an alkali metal carbonate and/or an alkali metal hydrogencarbonate to be used according to the invention is advantageously sprayed as finely divided droplets (atomized, dispersed).

When these are contacted with the rising acrylic acid vapor, the acrylic acid is taken up into the finely divided aqueous droplets which preferably have a very low temperature. The aqueous alkali metal acrylate solution which forms collects on the chimney tray and may be continuously withdrawn from it. Droplet sizes of, for example, from 0.1 to 5 mm, preferably from 0.3 to 1 mm, may be applied. The atomized aqueous solution of basic alkali metal salt to be used according to the invention in the above-outlined procedure preferably has a temperature in the range from 10 to 60_C, more preferably in the range from 20 to 45_C.

To atomize the aqueous alkali metal salt solution, atomizer nozzles, for example, may be used, as described, for example, by DE-A 19924533.

The aqueous alkali metal solution, advantageously precooled, may be fed to such nozzles, for example, under pressure. The aqueous alkali metal solution may be dispersed in such a manner that it is decompressed in the nozzle orifice once it has reached a certain minimum velocity. The abovementioned purpose may also be fulfilled by one-material nozzles, for example whirl chambers (hollow or full cone nozzles) (for example from Düsen-Schlick GmbH, DE, or from Spraying Systems Deutschland GmbH).

According to the invention, the atomization of the aqueous alkali metal salt solution may also be carried out by passing a concentrated aqueous alkali metal salt solution through a nozzle and passing a dilute aqueous alkali metal salt solution or water through another nozzle. Precise adjustment of the ratio of the two spray amounts allows the degree of neutralization to be set as desired.

Alternatively, the aqueous alkali metal salt solution to be used according to the invention may also be atomized using impingement atomizers. In impingement atomizers, the atomization is effected by at least one stream of aqueous alkali metal salt solution impinging upon at least one second stream of aqueous alkali metal salt solution and/or water and/or upon an impingement plate.

According to the invention, preference is given to impingement atomizers in which the atomization is effected by at least one stream of aqueous alkali metal salt solution impinging upon an impingement plate (for example of steel) (impingement plate atomizer).

The stream of aqueous alkali metal salt solution directed toward the impingement plate may have a flow velocity of, for example, from 20 to 80 km/h.

The aqueous solution of a basic alkali metal salt to be used according to the invention is advantageously conveyed in simple pipes (for example of steel) which are preferably tapered toward the end.

According to the invention, the separation between the outlet orifice of the pipe and the impingement plate is advantageously frequently from 5 to 30 cm, in many cases from 10 to 20 cm. The size and shape of the impingement plate may vary within a wide range. In general, the impingement plate is round and its diameter is frequently from 1 to 20 times, frequently from 1 to 5 times, the diameter of the outlet orifice of the pipe.

Normally, the impingement plate is flat. However, the impingement plate may also be concave or convex.

It will be appreciated that when the principle of impingement atomization is applied, it is also possible for a concentrated aqueous alkali metal salt solution and a dilute aqueous alkali metal salt solution or water to impinge upon each other.

The aqueous solution of a basic alkali metal salt to be used according to the invention has two purposes. Its cold content serves the purpose of direct cooling of the gaseous acrylic acid and of taking up the heat of neutralization. The basic aqueous solution of the alkali metal salt per se furthermore serves to take up the acrylic acid from the gas phase so as to form an aqueous alkali metal acrylate solution. This immediate generation of an aqueous alkali metal acrylate solution may also be referred to as quenching of acrylic acid in an aqueous basic alkali metal salt solution (quenching liquid). In general, the salt content of the quenching liquid will be from 10 to 60% by weight, frequently from 30 to 50% by weight or from about 30 to 40% by weight.

According to the invention, the aqueous alkali metal acrylate solution generated according to the invention will not be completely withdrawn from the distillation apparatus. Rather, it is advantageous to cool a portion (for example by means of plate heat exchangers) to support the cooling and condensation effect and to recycle it cooled as a further quenching liquid into the distillation apparatus. Advantageously, the recycling temperature according to the invention is from 10 to 60_C, preferably from 15 to 50_C and more preferably from 20 to 45_C.

It will be appreciated that the aqueous solution of a basic alkali metal salt required according to the invention may be combined with the above-described quenching liquid and these may subsequently be sprayed together as a quenching liquid. Impingement atomization may also be operated with the two quenching liquids.

Up to 90% of the amount of aqueous alkali metal acrylate solution formed may be recycled.

According to the invention, preference is given to carrying out the process according to the invention continuously. According to the invention, preference is given to immediately taking up the acrylic acid removed in the distillation apparatus from the gas phase into an aqueous solution of an alkali metal hydroxide, an alkali metal carbonate and/or an alkali metal hydrogencarbonate immediately within the apparatus intended for the subsequent polymerization (for example in a polymerization tank).

According to the invention, it is advantageous that the generation according to the invention of the aqueous alkali metal acrylate solution is quasi-in situ.

This is advantageous in that it opens up the possibility of completely dispensing with intermediate addition of polymerization inhibitor when the aqueous alkali metal acrylate solution is reused immediately. In this case, the required amount of free radical polymerization initiator is added to the aqueous alkali metal acrylate solution formed and the desired superabsorber resin is generated by free radical polymerization in a manner known per se. The lack of a polymerization inhibitor allows polymerization initiation using a comparatively small amount of free radical polymerization initiator. This reduction in starting amounts (both for the polymerization initiator and the polymerization inhibitor) results in a procedure which is more economical overall. The possibility of completely excluding any polymerization inhibitor in addition allows the production of qualities of superabsorber which were previously unattainable. The process described also allows the diacrylic acid content to be minimized until the start of the polymerization.

The amount of aqueous solution of a basic alkali metal salt to be used according to the invention is frequently such that the degree of neutralization in the resulting aqueous acrylate solution is at least 25 mol %, frequently at least 30 mol % and in many cases at least 33 mol %, based on the molar amount of acrylic acid contained therein. It will be appreciated that the alkali metal salt used for neutralization may also be used in a molar excess, based on the molar amount of acrylic acid contained therein. Such an excess will generally not exceed a value of 10 mol % or of 5 mol %, based on the molar amount of acrylic acid contained therein. From an application point of view, it is advantageous in many cases in the process according to the invention to set a degree of neutralization of the aqueous alkali metal acrylate solution of from 30 to 70 mol %.

It will be appreciated that the aqueous alkali metal acrylate solution generated according to the invention does not necessarily have to be fed directly to a free radically initiated polymerization. Rather, the possibility also exists of intermediately storing the aqueous alkali metal acrylate solution generated according to the invention before its further use for polymerization purposes.

From the point of view of "undesired free radical polymerization" and also "diacrylic acid formation", it is noticeable that the aqueous alkali metal acrylate solution generated according to the invention advantageously comprises the acrylic acid monomers in diluted form. It is further advantageous that such aqueous alkali metal acrylate solutions may be strongly cooled without any solid formation (freezing point depression; pure acrylic acid has a solidifying point at atmospheric pressure of about 13_C).

This is advantageous in particular when free radical storage inhibitors are added to the aqueous alkali metal acrylate solution generated according to the invention for the purposes of storage with increased reliability (for example amines, nitro compounds, phosphorus or sulfur compounds, hydroxylamines, N-oxides and quinones). For example, useful polymerization inhibitors include all of those cited in DE-A 10053086.

In this context, the use of the monomethyl ether of hydroquinone in particular has proven useful.

The increased dilution of the aqueous alkali metal acrylate solution and also increased reduction of the possible storage temperature without solid precipitation are accompanied by a reduced need for storage inhibitor for reliable storage.

Solid formation, in particular of the optionally neutralized acrylic acid present, is to be avoided because such solid precipitation is accompanied both by an increase in acrylic acid concentration and also a depletion of polymerization inhibitor in the acrylic acid. Particularly when crystalline acrylic acid is subsequently melted, this may lead to explosive, undesired spontaneous polymerization of acrylic acid.

In general, it is sufficient to add from 10 to 250 ppm by weight of storage polymerization inhibitor, frequently from 20 to 60 ppm by weight, to the aqueous alkali metal acrylate solutions obtainable according to the invention. This is true in particular when the storage polymerization inhibitor used is the monomethyl ether of hydroquinone (MEHQ).

When the intention is to use storage polymerization inhibitors, these are advantageously added to the aqueous solution of basic alkali metal salt already used as a quenching liquid in the process according to the invention.

The free radical polymerization of the aqueous alkali metal acrylate solution obtainable according to the invention for producing superabsorbers may otherwise be effected in a manner known per se, for example as described in U.S. Pat. No. 4,666,983, EP-A 785224, U.S. Pat. No. 4,286,082 and EP-A 785223.

In other words, at least 50% of the total weight of the monomers contained in the aqueous monomer composition to be free radically polymerized will generally comprise partially or completely neutralized acrylic acid. Up to 50% of the total weight of the monomers contained therein may therefore optionally comprise monomers copolymerizable with acrylic acid.

These copolymerizable monomers may also have more than one ethylenically unsaturated double bond, and these double bonds may also be conjugated to one another. In general, a copolymerizable monomer contains not more than 5 ethylenically unsaturated double bonds. The amount of these crosslinking monomers, based on the total amount of monomers contained in the aqueous monomer composition, will generally not be more than 30% by weight.

The copolymerizable monomers may be added to the aqueous alkali metal acrylate solution obtainable according to the invention either subsequently and/or at the same time as it is generated. For example, they may already be present dissolved in the aqueous alkali metal salt solution to be used as a quenching liquid according to the invention.

The free radical polymerization may, as mentioned at the outset, be carried out either as a solution polymerization or else as a suspension polymerization. In general, this gives a hydrogel which is converted to a hydrogel-forming powder and is generally finally surface postcrosslinked.

In a common embodiment, the polymerization is carried out as a solution polymerization while utilizing the Trommsdorff-Norrish effect.

Customarily, from 10 to 70% of the weight, frequently from 20 to 60% of the weight, of the aqueous monomer mixture to be free radically polymerized will be monomers.

The aqueous monomer mixture is used in partially or completely neutralized form. In general, the degree of neutralization of all acid group-carrying monomers will be from 20 to 100 mol %, based on the total molar amount of acid groups. The abovementioned degree of neutralization will often be from 50 to 100 mol % or from 90 to 100 mol %. If necessary, the degree of neutralization may be adjusted after the aqueous solution according to the invention is generated by adding, for example, a mineral acid or (advantageously polymerization-inhibited) acrylic acid.

In general, the polymerization will be carried out under substantial or complete exclusion of oxygen. Customarily, operation is effected under an inert gas atmosphere. The inert gas is in particular nitrogen. It has proven useful to purge the aqueous monomer mixture to be polymerized before and/or during polymerization with inert gas. However, particularly when the aqueous monomer mixture has none of the storage polymerization inhibitor stemming from the acrylic acid formed, the polymerization may also be carried out in the presence of oxygen, i.e. advantageously under air. The polymerization may, for example, be carried out in the temperature range from 0_C to 150_C or in the range from 0_C to 100_C. The polymerization may also be carried out either at atmospheric pressure or else under elevated or reduced pressure.

Examples of monoethylenically unsaturated monomers which are copolymerizable with acrylic acid and likewise have an acid group or the corresponding anhydride group include monoethylenically unsaturated mono- and dicarboxylic acids preferably having from 4 to 8 carbon atoms such as methacrylic acid, ethacrylic acid, α-chloroacrylic acid, crotonic acid, maleic acid, maleic anhydride, itaconic acid, citraconic acid, mesaconic acid, glutaconic acid, aconitic acid and fumaric acid; monoesters of monoethylenically unsaturated dicarboxylic acids having from 4 to 10, preferably from 4 to 6, carbon atoms, for example of maleic acid, such as monomethyl maleate; monoethylenically unsaturated sulfonic acids and phosphonic acids, for example vinylsulfonic acid, allylsulfonic acid, sulfoethyl acrylate, sulfoethyl methacrylate, sulfopropyl acrylate, sulfopropyl methacrylate, 2-hydroxy-3-acryloxypropylsulfonic acid, 2-hydroxy-3-methacryloxypropylsulfonic acid, styrenesulfonic acid, 2-acrylmido-2-methylpropanesulfonic acid, vinylphosphonic acid and allylphosphonic acid, and the salts, in particular the sodium, potassium and ammonium salts, of the acids mentioned.

Preferred monoethylenically unsaturated comonomers carrying acid groups include methacrylic acid, vinylsulfonic acid, 2-acrylamido-2-methylpropanesulfonic acid and mixtures of these acids or their salts.

The proportion of the abovementioned comonomers, based on the total amount of monomers, may be from 0.1 to 30, or from 0.5 to 20, % by weight.

To optimize the properties of the superabsorbers, it may be sensible also to use monoethylenically unsaturated comonomers which carry no acid groups. These include, for example, monoethylenically unsaturated nitriles such as acrylonitrile and methacrylonitrile, the amides of the abovementioned monoethylenically unsaturated carboxylic acids, for example acrylamide and methacrylamide, N-vinylamides such as N-vinylformamide, N-vinylacetamide, N-methylvinylacetamide, N-vinylpyrrolidone and N-vinylcaprolactam. These also include vinyl esters of saturated $C_1$–$C_4$-carboxylic acids such as vinyl formate, vinyl acetate and vinyl propionate, alkyl vinyl ethers having at least two carbon atoms in the alkyl group, for example ethyl vinyl ether or butyl vinyl ether, esters of monoethylenically unsaturated $C_3$–$C_6$-carboxylic acids, for example esters of monovalent $C_1$–$C_{18}$-alcohols and acrylic acid, methacrylic acid or maleic acid, acrylic and methacrylic esters of alkoxylated monohydric, saturated alcohols, for example of alcohols having from 10 to 25 carbon atoms which have been reacted with from 2 to 200 mol of ethylene oxide and/or propylene oxide per mole of alcohol, and also monoacrylic and monomethacrylic esters of polyethylene glycol or polypropylene glycol, and the number average molar masses may be, for example, up to 2000.

Further suitable acid group-free monoethylenically unsaturated comonomers include styrene and alkyl-substituted styrenes such as ethylstyrene or tert-butylstyrene.

The proportion of acid group-free monoethylenically unsaturated comonomers in the superabsorber resins will generally not exceed 20% by weight (the term acid groups in this context always includes the conjugated base group).

Useful crosslinking polyethylenically unsaturated comonomers are in particular those monomers which have 2, 3, 4 or 5 ethylenically unsaturated double bonds in the molecule which may also be conjugated to each other. These monomers are referred to here as crosslinking monomers. Examples of useful crosslinking monomers include N,N'-methylenebisacrylamide, polyethylene glycol diacrylates and polyethylene glycol dimethacrylates, each of which is derived from polyethylene glycols of number average molecular weight from 106 to 8500, preferably from 400 to 2000, trimethylolpropane triacrylate, trimethylolpropane trimethacrylate, ethylene glycol diacrylate, ethylene glycol dimethacrylate, propylene glycol diacrylate, propylene glycol dimethacrylate, butanediol diacrylate, butanediol dimethacrylate, hexanediol diacrylate, hexanediol dimethacrylate, diethylene glycol diacrylate, diethylene glycol dimethacrylate, triethylene glycol diacrylate, triethylene glycol dimethacrylate, dipropylene glycol diacrylate, dipropylene glycol dimethacrylate, tripropylene glycol diacrylate, tripropylene glycol dimethacrylate, allyl methacrylate, diacrylates and dimethacrylates of block copolymers of ethylene oxide and propylene oxide, esterified polyhydric alcohols such as glycerol, trimethylolpropane, pentaerythritol or dipentaerythritol, each of which has been di-, tri-, tetra- or pentaesterified with acrylic acid or methacrylic acid, esters of monoethylenically unsaturated carboxylic acids with ethylenically unsaturated alcohols such as allyl alcohol, cyclohexanol and dicyclopentyl alcohol, for example allyl acrylate and allyl methacrylate, and also triallylamine, dialkyldiallylammonium halides such as dimethyldiallylammonium chloride and diethyldiallylammonium chloride, tetraallylethylenediamine, divinylbenzene, diallyl phthalate, polyethylene glycol divinyl ethers of polyethylene glycols of number average molecular weight of from 106 to 4000, trimethylolpropane diallyl ether, butanediol divinyl ether, pentaerythritol triallyl ether, reaction products of 1 mol of ethylene glycol diglycidyl ether or of polyethylene glycol diglycidyl ether with 2 mol of pentaerythritol triallyl ether or of allyl alcohol, and divinylethyleneurea. Superabsorbers customarily comprise from 0.01 to 5% by weight, frequently from 0.2 to 3% by weight, of copolymerized crosslinking monomers.

Other useful crosslinking compounds include saturated or unsaturated polyfunctional compounds which have at least two (for example 2, 3, 4 or 5) functional groups which are complementary with regard to their reactivity toward the carboxyl group of acrylic acid or its alkali metal salt.

However, it will be appreciated that useful crosslinkers also include monoethylenically unsaturated compounds which, in addition to their ethylenically unsaturated double bond, have one further functional group which is complementary toward carboxyl groups. Examples thereof include hydroxyalkyl acrylates, hydroxyalkyl methacrylates and also glycidyl esters of (meth) acrylic acid. Further useful crosslinkers include polymers having a multiplicity of such complementary functional groups. Examples of useful complementary functional groups include hydroxyl, amino, epoxy and aziridine groups, and also isocyanate, ester and amido groups and alkoxysilyl groups. Examples of useful crosslinkers of this type include aminoalcohols such as ethanolamine or triethanolamine, di- and polyols such as 1,3-butanediol, 1,4-butanediol, ethylene glycol, diethylene glycol, triethylene glycol, tetraethylene glycol, polyethylene glycol, glycerol, polyglycerol, propylene glycol, polypropylene glycol, trimethylolpropane, pentaerythritol, polyvinyl alcohol, sorbitol, starch, block copolymers of ethylene oxide and propylene oxide, polyamines such as ethylenediamine, diethylenetriamine, triethylenetetramine, tetraethylenepentamine, pentaethylenehexamine and polyethyleneimines and also polyamines having number average molar masses each of up to 4,000,000, esters such as sorbitan fatty acid esters, ethoxylated sorbitan fatty acid esters, polyglycidyl ethers such as ethylene glycol diglycidyl ether, polyethylene glycol diglycidyl ether, glycerol glycidyl ether, glycerol polyglycidyl ether, diglycerol polyglycidyl ether, polyglycerol polyglycidyl ether, sorbitol polyglycidyl ether, pentaerythritol polyglycidyl ether, propylene glycol diglycidyl ether and polypropylene glycol diglycidyl ether, polyaziridine compounds such as 2,2-bishydroxymethylbutanol tris [3-(1-aziridinyl)propionate], diamides of carbonic acid such as 1,6-hexamethylenediethyleneurea and diphenylmethanebis-4,4'-N,N'-diethyleneurea, haloepoxy compounds such as epichlorohydrin and α-methylepifluorohydrin, polyisocyanates such as 2,4-tolylene diisocyanate and hexamethylene diisocyanate, alkylene-carbonates such as 1,3-dioxolan-2-one and 4-methyl-1,3-dioxolan-2-one, and also bisoxazolines and oxazolidones, polyamidoamines and their reaction products with epichlorohydrin, and also polyquaternary amines such as condensation products of dimethylamine with epichlorohydrin, homo- and copolymers of diallyldimethylammonium chloride and homo- and copolymers of dimethylaminoethyl (meth)acrylate which may optionally have been quaternized using, for example, methyl chloride.

Useful polymerization reactors include those customary for preparation, in the case of solution polymerization in particular belt reactors, extruders and kneaders. The polymers may in particular also be prepared by a continuous or batchwise kneading process.

In principle, useful initiators include any compounds which decompose when heated to polymerization temperature to form radicals. The polymerization may also be set off by the action of high-energy radiation, for example UV radiation, in the presence of photoinitiators. Initiation of the polymerization by the action of electron beams on the polymerizable aqueous mixture is also possible.

Examples of useful initiators include peroxo compounds such as organic peroxides, organic hydroperoxides, hydrogen peroxide, persulfates, perborates, azo compounds and redox initiator systems. Preference is given to water-soluble initiators. In many cases, it is advantageous to use mixtures of different polymerization initiators, for example mixtures of hydrogen peroxide and sodium peroxodisulfate or potassium peroxodisulfate. Examples of useful organic peroxides include acetylacetone peroxide, methyl ethyl ketone peroxide, tert-butyl hydroperoxide, cumene hydroperoxide, tert-amyl perpivalate, tert-butyl perpivalate, tert-butyl perneohexanoate, tert-butyl perisobutyrate, tert-butyl per-2-ethylhexanoate, tert-butyl perisononanoate, tert-butylpermaleate, tert-butyl perbenzoate, di (2-ethylhexyl) peroxydicarbonate, dicyclohexyl peroxydicarbonate, di(4-tert-butylcyclohexyl) peroxydicarbonate, dimyristyl peroxydicarbonate, diacetyl peroxydicarbonate, allyl peresters, cumyl peroxyneodecanoate, tert-butyl per-3,5,5-trimethylhexanoate, acetylcyclohexylsulfonyl peroxide, dilauroyl peroxide, dibenzoyl peroxide and tert-amyl perneodecanoate. Particularly useful polymerization initiators are water-soluble azo initiators, for example 2,2'-azo-bis(2-amidinopropane) dihydrochloride, 2,2'-azo-bis(N,N'-dimethylene)isobutyramidine dihydrochloride, 2-(carbamoylazo) isobutyronitrile, 2,2'-azobis[2-(2'-imidazolin-2-yl)propane] dihydrochloride and 4,4'-azobis(4-cyanovaleric acid). The polymerization initiators mentioned are used in customary amounts, for example in amounts of from 0.01 to 5, preferably from 0.05 to 2.0, % by weight, based on the monomers to be polymerized.

Preferred redox initiator systems are water-soluble and comprise as oxidizing component at least one of the abovementioned peroxo compounds and, as the reducing component, for example, ascorbic acid, glucose, sorbose, and ammonium or alkali metal sulfite, hydrogensulfite, thiosulfate, hyposulfite, pyrosulfite or sulfide, or a metal salt such as an iron (II) ions or sodium hydroxymethylsulfoxylate. Preference is given to using ascorbic acid or sodium sulfite as the reducing component of the redox initiator system. Based on the molar amount of monomers used in the polymerization, for example, from $3 \times 10^{-6}$ to 1 mol % of the reducing component of the redox initiator system and from 0.001 to 5.0 mol % of the oxidizing component of the redox initiator system are used.

When the polymerization is set off by the action of high-energy radiation, the initiators used are customarily photoinitiators.

The production of a superabsorber may also comprise a subsequent internal crosslinking of the gel. In the subsequent crosslinking (gel crosslinking), polymers which have been prepared by polymerization of at least partially neutralized acrylic acid, optionally with comonomers, are reacted with compounds which have at least two groups which are reactive toward the carboxyl groups. This reaction may be effected at room temperature or at elevated temperatures of up to 220_C. For subsequent internal crosslinking (gel crosslinking), the crosslinkers are added to the polymers obtained in amounts of from 0.5 to 20% by weight, preferably from 1 to 14% by weight, based on the amount of polymer.

The polymers obtainable as described are generally obtained as hydrogels. Their moisture content is generally in the range from 20 to 80% by weight. The hydrogel obtained in this manner is then converted in a manner known per se to a hydrogel-forming powder and finally it is generally surface postcrosslinked.

To this end, the hydrogel resulting from the polymerization is generally initially comminuted by known methods. The rough comminution of the hydrogels is effected by means of customary tearing and/or cutting tools, for example by the action of a discharge pump in the case of polymerization in a cylindrical reactor or by a cutting roller or cutting roller combination in the case of belt polymerization.

The partially or completely neutralized polymer obtained in this way is then dried by known processes at elevated temperature, for example in the range from 80_C to 250_C and in particular in the range from 100_C to 180_C. This provides the polymers in the form of powders or granules which may optionally be subjected to one or more milling and sieving procedure to adjust the particle size.

The subsequent surface postcrosslinking is effected in a manner known per se using the dried, preferably milled and sieved, polymer particles obtained in this manner. Surface postcrosslinking is effected using compounds which have at least two functional groups which can react with the functional groups, preferably the carboxyl groups, of the polymer with crosslinking (postcrosslinkers). To this end, the postcrosslinkers, preferably in the form of an aqueous solution, are applied to the surface of the polymer particles. The aqueous solution may comprise water-miscible organic solvents. Examples of useful solvents include $C_1$–$C_4$-alcohols such as methanol, ethanol and isopropanol, or ketones such as acetone and methyl ethyl ketone.

Examples of useful postcrosslinkers include:
- di- or polyglycidyl compounds such as phosphonic acid diglycidyl ether or ethylene glycol diglycidyl ether, bischlorohydrin ethers of polyalkylene glycols,
- alkoxysilyl compounds,
- polyaziridines, compounds comprising aziridine units and based on polyethers or substituted hydrocarbons, for example bis-N-aziridinomethane,
- polyamines or polyamidoamines and also their reaction products with epichlorohydrin,
- diols and polyols, for example ethylene glycol, 1,2-propanediol, 1,4-butanediol, glycerol, methyl triglycol, trimethylolethane, trimethylolpropane, polyethylene glycols having an average molecular weight $M_w$ of from 200 to 10,000, di- and polyglycerol, pentaerythritol, sorbitol, the ethoxylates of these polyols and also their esters with carboxylic acids or with carbonic acid such as ethylene carbonate or propylene carbonate,
- carbonic acid derivatives such as urea, thiourea, guanidine, dicyanodiamide, 2-oxazolidinone and its derivatives, bisoxazoline, polyoxazolines, di- and polyisocyanates,
- di- and poly-N-methylol compounds, for example methylenebis(N-methylolmethacrylamide) or melamine-formaldehyde resins, and
- compounds having two or more block isocyanate groups, for example trimethylhexamethylene diisocyanate blocked with 2,2,3,6-tetramethylpiperidinone-4.

If required, acid catalysts such as p-toluenesulfonic acid, phosphoric acid, boric acid or ammonium dihydrogenphosphate may be added.

Preference is given to applying the crosslinker solution by spraying on a solution of the crosslinker in conventional mixers or mixing and drying apparatus, for example Patterson-Kelly mixers, DRAIS turbulence mixers, Lödige mixers, screw mixers, plate mixers, fluidized bed mixers and Schugi-Mix. The spraying-on of the crosslinking solution may be followed by a temperature treatment step. This is preferably effected in a downstream drier and at a temperature of from 80 to 230_C, more preferably from 80 to 190_C and most preferably from 100 to 160_C, and over a period of from 5 minutes to 6 hours, preferably from 10 minutes to 2 hours and more preferably from 10 minutes to 1 hour, which may remove both cleavage products and solvent fractions. However, the drying may also be effected in the mixer itself, for example by heating the jacket or by blowing in a preheated carrier gas.

Before the aqueous alkali metal acrylate solution obtainable according to the invention is used for polymerization purposes, it may also be extracted using an organic solvent which has limited water solubility or is water-immiscible. In this manner, interfering impurities, for example low molecular weight aldehydes of any kind, still contained in the aqueous alkali metal acrylate solution may be removed.

An organic solvent having limited miscibility with water includes in particular those organic solvents whose solubility in water at 20_C and 1 atm is less than 10% by weight, preferably less than 7% by weight and more preferably less than 5% by weight.

Examples of such solvents are aliphatic and cycloaliphatic hydrocarbons such as hexane, heptane, octane, their isomers and cyclohexane, aromatic hydrocarbons such as toluene, xylenes, ethylbenzene and cumene, technical grade hydrocarbon mixtures such as petroleum ether, petroleum fractions and the like, esters of aliphatic $C_1$–$C_4$-carboxylic acids with $C_1$–$C_6$-alkanols or with cycloalkanols and preferably having from 4 to 10, in particular from 5 to 8, carbon atoms, such as n-butyl and isobutyl formate, ethyl acetate, n-propyl acetate, isopropyl acetate, n-butyl acetate, isobutyl acetate, amyl acetate, isoamyl acetate, n-hexyl acetate, cyclohexyl acetate, methyl, ethyl, n-propyl, isopropyl, n-butyl and isobutyl propionate, methyl, ethyl, n-propyl, isopropyl, n-butyl and isobutyl butyrate and isobutyrate, aliphatic and cycloaliphatic ketones having at least 5 carbon atoms such as methyl propyl ketone, methyl isopropyl ketone, methyl butyl ketone, methyl isobutyl ketone, methyl amyl ketone, methyl isoamyl ketone, diethyl ketone, ethyl propyl ketone, ethyl butyl ketone, diisopropyl ketone, diisobutyl ketone, cyclohexanone and trimethylcyclohexanone, aliphatic and cycloaliphatic ethers having at least 4 carbon atoms such as diethyl ether, methyl tert-butyl ether, diisopropyl ether, di-n-butyl ether and ethyl tert-butyl ether, chlorinated hydrocarbons such as dichloromethane, chloroethane, dichloroethane and trichloroethane, and also mixtures of the abovementioned solvents.

Preference is given to those solvents whose boiling point is less than 150_C and in particular less than 140_C at atmospheric pressure (1 atm). Preference is given to those solvents whose solvent polarity by an $E_T(30)$ value according to C. Reichardt et al. (Liebigs Annalen der Chemie, 1983, p. 721–743) is in the range from 32 to 42 kcal/mol and in particular in the range from 33 to 40 kcal/mol.

Particularly preferred solvents are methyl tert-butyl ether, toluene, ethyl acetate, isobutyl acetate and methyl isobutyl ketone.

The aqueous alkali metal acrylate solution may be extracted either continuously or batchwise. The extraction may be effected using, for example, the extraction apparatus as known from the prior art (see, for example, Ullmanns Enzyklopädie der Techn. Chem., 4th ed., Vol. 2, p. 560ff, Verlag-Chemie Weinheim; Ullmann's Encyclopedia of Ind. Chem. 5th ed. on CD-Rom, "Liquid-liquid extraction 3.1", Wiley-VCH Weinheim 1997; Vauck/Müller, "Grundoperationen chemischer Verfahrenstechnik", 10th ed., Deutscher Verlag für Grundstoffindustrie Leipzig, Stuttgart, 1994, p. 777–796). Examples of useful solvent extractors include stirred extractors, centrifugal pump extractors, jet pump extractors, ultrasound extractors (which are preferably arranged as extraction batteries), mixer-settler apparatus, extraction columns having stationary internals (for example randomly packed columns, sieve tray columns and cascade tray columns) and/or having means for pulsation or having moving internals (for example stirred columns, rotating disk columns and swirl columns) and also centrifugal extractors.

The extractors used for the extraction process are preferably designed in such a manner that the theoretical number of plates is at least 3, preferably at least 5. This number of plates is customarily not more than 15. Most frequently, this number of plates is in the range from 5 to 10.

After the extraction step and the separation of the extract and the aqueous raffinate, the degree of neutralization may optionally be readjusted to the value required for the particular application of the aqueous alkali metal acrylate solution. For example, the degree of neutralization may be reduced by adding a mineral acid or acrylic acid, or increased by adding a base such as an alkali metal hydroxide, alkali metal carbonate or alkali metal hydrogencarbonate.

The organic solvent (extract) resulting from the extraction may be worked up distillatively in a simple manner. In this manner, the solvent is recovered and may be recycled into the extraction.

The process according to the invention is applicable in particular to acrylic acid-containing mixtures which, based on their total weight, comprise at least 70% by weight of acrylic acid. In other words, the process according to the invention is applicable when the above-described acrylic acid content is at least 80% by weight, or at least 90% by weight, or at least 95% by weight, or at least 97% by weight or at least 99% by weight.

The process according to the invention is therefore applicable in particular to the acrylic acid-containing mixtures which have been treated distillatively for the purposes of removing acrylic acid in EP-A 717029, EP-A 839790, U.S. Pat. No. 5,482,597, EP-A 713854, DE-A 19634614, U.S. Pat. No. 5,710,329, EP-A 1110940, DE-A 19853064, DE-A 4201697, DE-A 3641996, EP-A 1033359, DE-A 10138150, DE-A 10138101 and EP-A 648732.

It will be appreciated that the acrylic acid-containing mixture to be treated in accordance with the invention is admixed with a process polymerization inhibitor for the purposes of the distillative treatment according to the invention. Useful process inhibitors include all of those which are recommended in the prior art, inter alia in the above-cited documents, for distillation purposes. Phenothiazine is a particularly suitable polymerization inhibitor. Based on the amount of acrylic acid contained therein, the amount of inhibitor is generally from 200 to 400 ppm by weight. For the purposes of additional polymerization inhibition, the process according to the invention is performed while additionally conducting frequently air or nitrogen-diluted air through the distillation apparatus and admixing the reflux with inhibitor.

Depending on the composition of the acrylic acid-containing mixture to be distilled, the distillation process according to the invention may be carried out using the distillation devices which are known per se. These may contain internals or be free of internals. Useful internals include structured packings, trays (for example dual-flow trays), random packings (for example Raschig rings) or any other possible internals. Where a distillation apparatus having internals, for example a column, is used, process polymerization inhibitor will generally also be conducted into the distillation apparatus below the withdrawal tray. The inhibitor may, for example, be added in acrylic acid of appropriate purity.

The application of the process according to the invention is recommended in particular for the final distillation step in the chains cited hereinbelow for preparing acrylic acid.

Propene, propane and/or acrolein are initially subjected in a manner known per se to heterogeneously catalyzed gas phase oxidation to acrylic acid. This may be carried out, for example, as described in the documents DE-A 19636489, WO-0196271, DE-A 10028582, DE-A 10122027, DE-A 10121592, DE-A 10119933, DE-A 10118814, DE-A 10101695, DE-A 10063162, DE-A 10051419, DE-A 10033121, DE-A 10028582, DE-A 19955176, DE-A 19955168, DE-A 19948523 and DE-A 19948248.

Acrylic acid is removed from the resulting product gas mixture either by absorption in an absorption liquid or by fractional condensation of the product gas mixture.

Useful absorption liquids are in principle all of those in which acrylic acid has a significant solubility. Among these, preference is given to those from which acrylic acid can be removed again at lowest cost and inconvenience by distillation. Examples of such solvents include water and organic liquids whose boiling temperatures at atmospheric pressure (1 atm) are above the boiling temperature of acrylic acid. Advantageous high-boiling organic liquids have a boiling point of $\geq 160\_C$ at 1 atm. Examples of useful high-boiling organic liquids include diphenyl, diphenyl ether, dimethyl phthalate, ethylhexanoic acid, N-methylpyrrolidone, paraffin fractions and mixtures thereof. The use of hydrophobic organic liquids in particular, as recommended by DE-A 2136396, DE-A 4436243 and DE-A 4308087, is advantageous. These include in particular high-boiling organic liquids of which at least 70% by weight comprise molecules which contain no externally active polar groups and, for example, are accordingly unable to form hydrogen bonds. Although the remarks made hereinbelow are generally valid, they apply in particular to the use of a mixture of from 70 to 75% by weight of diphenyl ether and from 25 to 30% by weight of diphenyl and also to the use of a mixture of from 70 to 75% by weight of diphenyl ether and from 25 to 30% by weight of diphenyl and, based on this mixture, from 0.1 to 25% by weight of o-dimethyl phthalate.

Advantageously, the absorption is carried out in countercurrent. It is further advantageous when the product gas mixture of the gas phase oxidation is cooled before the absorption. This may be effected by direct and/or indirect cooling. Direct cooling may be realized, for example, as described in DE-A 10063161, or in DE-A 2449780 or in DE-A 4308087 by partial evaporation of a high-boiling cooling liquid (preference is given to using the later absorption liquid) in a direct condenser (quenching apparatus).

The subsequent absorption itself may be carried out, for example, as described in DE-A 10115277, EP-A 1125912, DE-B 2136396, DE-A 19838817, DE-A 4436243 and DE-A 4308087.

Crude acrylic acid may then be removed from the resulting absorbate as described in DE-A 19838783, DE-A 19838795, DE-A 19838817, DE-A 10115277 and DE-A 19606877 by a rectificative route.

An alternative process for removing crude acrylic acid from the product gas mixture of a heterogeneously catalyzed gas phase oxidation is offered by fractional condensation of the product gas mixture, as described in DE-A 10217121, DE-A 10053086, DE-A 19924533 and DE-A 19909929.

When the crude acrylic acid obtained in this manner still has a marked impurity content, it may initially be fed to a crystallization for the purposes of further purification. The crystallization process to be applied which in general comprises only one purification stage is subject to no restriction. In other words, it may be either a layer crystallization (for example a dynamic layer crystallization, for example falling-film crystallization or a static layer crystallization on immersed cooled surfaces) or a suspension crystallization. The resulting acrylic acid shall likewise be referred to hereinbelow as crude acrylic acid.

The crude acrylic acids obtainable as described above generally have an intolerable content of aldehydic impurities for the subsequent acrylic acid uses described in this document.

Advantageously, such crude acrylic acid is accordingly first treated with an aldehyde scavenger. The aldehyde scavenger may be added directly into a line which is used to feed the crude acrylic acid to further work-up or into a delay tank in which the crude acrylic acid is intermediately stored before it is fed to further work-up.

Useful aldehyde scavengers include all compounds which convert the aldehydes present in the crude acrylic acid substantially quantitatively to compounds having a higher boiling point than acrylic acid. For this purpose, nitrogen compounds having at least one primary amino group are particularly suitable (cf. EP-A 648732, EP-A 717029, EP-A 713854, U.S. Pat. No. 5,482,597, EP-A 1110940 and DE-A 3641996). Examples include aminoguanidine salts, hydrazine, alkyl- and arylhydrazines, carboxylic hydrazides and aminophenols. Among these, particular preference is given to aminoguanidine hydrogencarbonate.

Preference is given to adding the aldehyde scavenger in an excess to the aldehyde contained in the crude acrylic acid, for example in an amount of from 1.5 to 2.5 mol of aldehyde. For the reaction with the aldehyde scavenger, a temperature of from 15 to 50_C, preferably from 20 to 30_C, is sufficient. Customarily, reaction times of from 10 minutes to 72 hours, preferably from 2 to 50 hours, are maintained.

When aminoguanidine hydrogencarbonate is used as the aldehyde scavenger, carbon dioxide is released and aminoguanidine hydrogenacrylate is initially formed. This reacts with the aldehyde groups of the aldehydes present to give the corresponding iminoguanidine derivatives or their rearrangement products. Treatment with the aldehyde scavenger allows the residual free aldehyde content of the crude acrylic acid, expressed as furfural, to be reduced to less than 20 ppm by weight, in particular to less than 5 ppm by weight and very particularly to less than 3 ppm by weight.

The crude acrylic acid treated as above may then be converted in various ways in accordance with the invention to an aqueous alkali metal acrylate solution.

In the simplest case, the treated crude acrylic acid is thermally separated in a distillation apparatus into acrylic acid-containing vapors and a high-boiling residue. The thermal separation may be effected by simple distillation, i.e. substantially without reflux or condensate, or rectificatively. In the former case, a distillation column without separating internals, i.e. a hollow column- or tower-like construction which has generally been manufactured from stainless steel, is advantageously used. In order to avoid droplets of crude acrylic acid being entrained by the acrylic acid-containing vapors, the column is advantageously equipped with a droplet separator of customary design, for example in the form of wire mesh packings having a large internal surface area, for example manufactured from chromium nickel steels, aluminum, polypropylene, polytetrafluoroethylene or the like, or in the form of a dumped packing or structured packing, for example a stack of corrugated metal sheets separated from each other and arranged parallel to the longitudinal axis of the column and having a small height of, for example, from 20 to 100 cm.

The liquid phase temperature is customarily from about 65 to 130_C, preferably from 70 to 100_C, and the column pressure from 50 to 120 mbar. The heating of the liquid phase of the column is effected by an external or internal circulation evaporator, preferably a Robert evaporator or a forced circulation-decompression evaporator. In evaporators of the Robert type, a heating element having vertical boiling tubes is mounted in a cylindrical evaporator element. The crude acrylic acid is inside the boiling tubes. The circulation within the tubes is effected by the rising vapor bubbles. To recycle the liquid conveyed upward, one or more downpipes are installed in the heating element.

Apart from the liquid phase heating described, preference is given to not actively heating the column; the column jacket is, however, preferably insulated in order to avoid excess heat loss through heat radiation. The absence of column heating (apart from the liquid phase heating) has the effect that droplets of crude acrylic acid which are entrained by acrylic acid-containing vapors are not heated on the way through the gas phase of the column and their size is not reduced by the evaporation of volatile constituents. The entrained droplets which retain their size or increase in size by coagulation may then be efficiently held back when the acrylic acid-containing vapors pass through a droplet separator.

Apart from the column jacket, the other parts of the plant which come into contact with the acrylic acid-containing vapors, in particular the lines in which the acrylic acid-containing vapors are conducted until their condensation, should be provided with trace heating in order to avoid undesired premature condensation. For example, the lines may be configured as jacketed pipes within whose annular space between the jacket and the pipe a heating medium is circulated. Alternatively, a pipe flowed through by heating medium which is in heat-transferring contact with the line which conducts the acrylic acid-containing vapors and is, for example, wound in a spiral around it or runs parallel to it, may be provided.

The distillation is generally conducted in such a manner that the residue makes up at least 8% by weight, for example from 8 to 30% by weight, preferably from 10 to 25% by weight, of the treated crude acrylic acid fed to the distillation column. In this manner, a residue is obtained which can be handled and does not have too high a viscosity. It has also been found that further evaporation leads to more significant fouling on the heat exchanger surfaces of the evaporator used for liquid-phase heating of the column which, within a short time interval, forces the shutdown and cleaning of the plant.

To recover acrylic acid still contained in the first residue, this is fed to a film evaporator to obtain a further amount of acrylic acid-containing vapors. A useful film evaporator is a wiped film evaporator. In this type, the liquid to be evaporated is distributed over a tube wall by a rotating arrangement of wipers. Particular preference is given to evaporators of the Sambay type. It has been found that, owing to the design, film evaporators show little tendency to fouling and thus allow a more rapid evaporation of the residue without cleaning interruption as is possible in the primary distillation column. The first residue is concentrated in the film evaporator preferably by from 35% to 5%, in particular by from 10% to 20%.

The second portion of vapors can be combined with the first portion of vapors, conveniently by recycling the second portion of vapors into the distillation column. Advantageously, the second portion of vapors is introduced below a droplet separator provided within the distillation column and the combined vapors are passed through the droplet separator. This procedure has the advantage that only a common droplet separator is required for removing entrained droplets from the first and second portions of vapor, which reduces the capital costs and the cost and inconvenience associated with the cleaning. The residues occurring on the film evaporator which correspond, for example, to from 0.5 to 5% by weight, generally from 1 to 2% by weight, of the total crude acrylic acid feed are disposed of.

In a preferred embodiment, the crude acrylic acid treated with the aldehyde scavenger before introduction into the distillation column is heated to a temperature of from 40 to 110_C, preferably from 50 to 60_C. The heating is conveniently effected by indirect heat exchange, for example by means of a heat exchanger with flow-through. The introduction of preheated crude acrylic acid into the distillation column has the advantage that a smaller amount of heat has to be applied in the column liquid phase via the evaporator provided for this purpose, which in turn leads to reduced fouling on its heat exchanger surfaces.

The thermal separation of the crude acrylic acid is advantageously carried out using a dissociation catalyst for oligomeric acrylic acid, in particular diacrylic acid, in particular acids such as alkyl- or arylsulfonic acid, for example dodecylbenzenesulfonic acid or p-toluenesulfonic acid, or bases such as sodium hydroxide or potassium carbonate. The dissociation catalyst is customarily used in an amount of from 0.5 to 10 kg per metric ton of crude acrylic acid. The dissociation catalyst may be added to the crude acrylic acid feed or to the feed of the film evaporator.

The acrylic acid-containing vapors are treated in accordance with the invention, i.e. immediately taken up from the gas phase into an aqueous solution of an alkali metal hydroxide, an alkali metal carbonate and/or an alkali metal hydrogencarbonate to form the desired polymerizable aqueous alkali metal acrylate solution.

When the removal of acrylic acid is carried out rectificatively, one or two stages may be used. When one stage is used, the essential difference to what has just been described is that the column contains internals (for example random packings, trays and/or structured packings).

When there are two stages, which is recommended in particular when the treated crude acrylic acid still comprises significant levels of low-boiling nonaldehydic secondary components such as acetic acid, formic acid, etc., these low-boiling components accompanied by acrylic acid may be removed overhead (and condensed conventionally) from the treated crude acrylic acid in a first rectification stage and this acrylic acid fraction may be further used for the purposes of preparing acrylic esters (for example methyl acrylate, ethyl acrylate, butyl acrylate, 2-ethylhexyl acrylate, etc.). The liquid phase would then be further treated distillatively and/or rectificatively as described above and the acrylic acid-containing vapors taken up immediately from the gas phase into an aqueous alkali solution in accordance with the invention.

However, the process according to the invention may also be applied to the processes for rectificative removal of (meth)acrylic acid described in DE-A 10218419.

The alkali metal acrylate solutions obtainable as described above are outstandingly suitable for immediate production of water-absorbing resins based on polyacrylates.

It will be appreciated that the distillation and/or rectification processes described will be carried out in the presence of process inhibitors such as phenothiazine. They are customarily present both in the feed to the columns and in the reflux (where present).

For the purposes of additional polymerization inhibition, oxygen-containing gases, for example air, will frequently be conducted through the columns.

To prevent fouling, the rectifications described are in many cases additionally carried out in the presence of organic sulfonic acids such as dodecylbenzenesulfonic acid and/or in the presence of surfactants, as described and recommended, for example, by EP-A 648732, EP-A 713854, U.S. Pat. No. 5,482,597, EP-A 839790, DE-A 19810962 and DE-A 4335172.

EXAMPLE 14 m$^3$ per hour of crude acrylic acid treated with aminoguanidine hydrogencarbonate and 60 kg of dodecylbenzenesulfonic acid are introduced at the 40th tray of a rectification column 1 containing 45 dual-flow trays (diameter of the drillholes=15 mm).

The composition of the untreated crude acrylic acid comprises:

98% by weight of acrylic acid,
250 ppm by weight of phenothiazine,
300 ppm by weight of furfurals,
50 ppm by weight of benzaldehyde,
50 ppm by weight of allyl acrylate,
150 ppm by weight of acetic acid,
350 ppm by weight of propionic acid,
1500 ppm by weight of water.

The amount of aminoguanidine hydrogencarbonate (AGHC) added to this crude acrylic acid is such that there are 2.0 mol per mole of aldehydes contained as secondary components in the crude acrylic acid.

The rectification column 1 is operated at a bottom pressure of 130 mbar and a bottom temperature of 86_C. To stabilize the column, 2.5 m$^3$ (STP) of air are conducted through the bottom of the column.

The column is polymerization-inhibited via its reflux (3 m$^3$/h).

To this end, a portion (200 l/h) of the top takeoff (low boiler-containing acrylic acid) is admixed with 1% of its weight of phenothiazine and added to the reflux. A further portion (150 l/h) of top takeoff comprising 1% of its weight of added phenothiazine is used to stabilize the top takeoff (1.4 m$^3$/h) not recycled into the column. This may be used for preparing alkyl esters of acrylic acid.

The condensation at the top of the column is effected by direct cooling (quenching circuit) by means of cooled (to a temperature of 30_C) top takeoff which has previously been removed and inhibited. The remaining offgas stream is washed to free it of acrylic acid by means of a downstream second quenching circuit operated with water at 18_C.

Each quenching space is closed off in the downward direction by a chimney tray. The washing water may be disposed of in a treatment plant. The term quenching circuit expresses the fact that a proportion of the condensate formed is passed through a heat exchanger, cooled and recycled into the column as an additional quenching liquid in the circuit to enhance the cooling effect.

The direct cooling may also be effected in a quenching space outside the rectification column 1.

The gas mixture is passed from above into this quenching space and conducted downward in cocurrent with the sprayed cooled quenching liquid (the condensation withdrawal is effected at the lower end). Just above the lower end, there is a side arm by which the offgas leaves the quench. In this side arm, the offgas is again washed by exposing it to the countercurrent of the spray drops of a second quench. The temperature level of the second quench is below the temperature level of the first quench. The quenching liquid used in each case is cooled, previously removed and inhibited top takeoff.

The liquid phase of the rectification column 1 is fed at a rate of 12 m³/h to a distillation column without internals. Its bottom temperature is 72_C at a bottom pressure of 78 mbar.

Overhead and downstream of a droplet separator, purified acrylic acid (≧99.5% by weight) is taken up in a quenching circuit in 25% by weight cooled aqueous NaOH solution at a rate of 11.7 m³/h. Heat of condensation and neutralization are removed via parallel plate heat exchangers of a total area of 600 m². The quenching circuit temperature is maintained at from 35 to 40_C. The sodium hydroxide solution metering is adjusted by means of a ratio control system in such a manner that 75% of the acrylic acid is neutralized. The liquid phase of the purifying column is concentrated in a downstream falling-film evaporator (75_C, 70 mbar) to 300 l/h and the vapors are recycled into the distillation column below the droplet separator. The remaining residue is disposed of by combustion.

The aqueous sodium acrylate solution withdrawn from the quenching circuit has a total content of acrylic acid and sodium acrylate of 40% by weight. Stabilization of the quenching circuit with 50 ppm by weight of a monoethyl ether of hydroquinone proves to be sufficient.

In a laboratory kneader, 6000 g of the aqueous sodium acrylate solution obtained, 27 g of polyethylene glycol (400) diacrylate, 16.7 g of sodium peroxodisulfate and 0.36 g of ascorbic acid are initially charged. Nitrogen is passed through the initial charge. The jacket temperature of the laboratory kneader is raised to 74_C. At the onset of the polymerization, in the course of which the temperature rises to 88_C, a solid gel forms which is then dried at 160_C, mechanically comminuted and sieved. A polymer powder of particle size from 100 to 800 ∝m is sieved out.

To determine the free swellability, 0.2 g of the dried polymer powder is weighed into a 60×85 mm teabag which is subsequently sealed. The teabag is then placed for 30 minutes in an excess of 0.9% by weight sodium chloride solution (at least 0.83 l of sodium chloride solution/g of polymer). The teabag is subsequently centrifuged at 250 g for 3 minutes. The liquid takeup is 37.4 g/g of polymer.

To determine the extractable fractions, 0.9 g of the dried polymer powder is suspended in 187 ml of 0.9% by weight aqueous sodium chloride solution in a beaker. The suspension is then filtered through a 0.22 ∝m filter and the content of extractables determined by acid-base titration.

It is 21.8% by weight.

We claim:

1. A process for preparing an aqueous alkali metal acrylate solution by distillatively removing acrylic acid from an acrylic acid-containing mixture and generating an aqueous alkali metal acrylate solution from the distillatively removed acrylic acid and an aqueous solution of a basic alkali metal salt, which comprises
    a) feeding the acrylic acid-containing mixture to a distillation apparatus,
    b) carrying out the removal of the acrylic acid from the acrylic acid-containing mixture in the distillation apparatus above the feed point and
    c) generating the aqueous alkali metal acrylate solution in such a manner that the acrylic acid removed in the distillation apparatus is taken up immediately from the gas phase into an aqueous solution of at least one alkali metal compound selected from the group consisting of an alkali metal hydroxide, an alkali metal carbonate and an alkali metal hydrogencarbonate.

2. The process as claimed in claim 1, wherein the alkali metal acrylate of said aqueous alkali metal acrylate solution, optionally with at least one comonomer polymerizable with said alkali metal acrylate, is subjected to polymerization to form a polyacrylate.

3. The process as claimed in claim 1, wherein the acrylic acid removed in the distillation apparatus is taken up immediately from the gas phase into said aqueous solution in a polymerization apparatus, and is polymerized in said apparatus.

4. The process as claimed in claim 1, wherein removal of the acrylic acid is carried out above a chimney tray mounted in the distillation apparatus, which chimney tray is configured in such a manner that although gas phases can rise through the chimney, no liquid phase can reflux through it into the distillation apparatus.

5. The process as claimed in claim 4, wherein the aqueous solution of said at least one alkali metal compound is atomized and sprayed as finely divided droplets, and the acrylic acid is taken up into said finely divided droplets.

6. The process as claimed in claim 5, wherein said finely divided droplets have a droplet size of from 0.1 to 5 mm.

7. The process as claimed in claim 6, wherein said finely divided droplets have a temperature of from 10 to 60° C.

8. The process as claimed in claim 5, wherein said atomizing is carried out with an impingement atomizer.

9. The process as claimed in claim 8, wherein said impingement atomizer contains an impingement plate, and the aqueous solution of said at least one alkali metal compound is directed toward the impingement plate at a flow velocity of from 20 to 80 km/h.

10. The process as claimed in claim 1, wherein a portion of the aqueous alkali metal acrylate solution is cooled and then recycled into the distillation apparatus.

11. The process as claimed in claim 10, wherein recycle is carried out at a temperature of from 10 to 60° C.

12. The process as claimed in claim 1, wherein said process is carried out continuously.

13. The process as claimed in claim 3, wherein a polymerization inhibitor is not added to the aqueous alkali metal acrylate solution.

14. The process as claimed in claim 1, wherein a free radical storage inhibitor is added to the aqueous alkali metal acrylate solution.

15. The process as claimed in claim 3, wherein polymerization is carried out in the presence of at least one comonomer polymerizable with acrylic acid.

16. The process as claimed in claim 15, wherein a superabsorber is formed as a product of said polymerization.

* * * * *